US00PP30074P2

(12) United States Plant Patent
Hansen

(10) Patent No.: US PP30,074 P2
(45) Date of Patent: Jan. 8, 2019

(54) ***LEUCANTHEMUM* PLANT NAMED 'CREAM PUFF'**

(50) Latin Name: ***Leucanthemum* x *superbum* (L. Burbank)**
Varietal Denomination: Cream Puff

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/731,780

(22) Filed: Jul. 31, 2017

(51) Int. Cl.
*A01H 5/02* (2018.01)

(52) U.S. Cl.
USPC ..... Plt./285

(58) Field of Classification Search
USPC ..... Plt./263.1, 284, 285
See application file for complete search history.

(56) References Cited

PUBLICATIONS 2017-2018 Walters Garden catalog. https://www.provenwinners.com/sites/provenwinners.com/files/images/professional/catalogs/1-intro-pw_perennials_2018.pdf. 3 pgs. (Year: 2017).*

* cited by examiner

*Primary Examiner* — Susan McCormick Ewoldt
*Assistant Examiner* — Karen M Redden

(57) ABSTRACT

The new Shasta daisy plant, *Leucanthemum* 'Cream Puff', is a sturdy plant with dark green serrated foliage and strong heavily-branched stems. The numerous freely-flowering inflorescences producing buds beginning with light yellow ray florets developing to cream surrounding gold center and cover the plant in a mound from the top of the plant to the ground. Flowering is repeated if deadheaded. The new plant is useful in the landscape as a long-flowering border, in mass, as accent plants and containerized for patio or indoor use, or as a cut flower.

1 Drawing Sheet

Botanical classification: *Leucanthemum* x *superbum* (L. Burbank).

Variety denomination: 'Cream Puff'.

BACKGROUND OF THE INVENTION

The original *Leucanthemum* x *superbum*, or Shasta daisies, were bred by Luther Burbank in the late 1800's as a cross between *Leucanthemum maximum* (Ramond) DC. with *Leucanthemum lacustre* (Broth.) Samp. The new plant, *Leucanthemum* 'Cream Puff' originated from a planned breeding program of the inventor at a wholesale perennial nursery in Zeeland, Mich., USA in the summer of 2011. The new *Leucanthemum* was a single plant selected from a group of seedlings from an open pollination of an unreleased proprietary hybrid female parent identified as K9-31-02 (not patented). The specific male parent is unknown but may have been any one of a number of siblings or hybrids from similar crosses in an isolated breeding region. The individual plant that eventually became 'Cream Puff' was first evaluated in the summer of 2013 and originally given the breeder number 11-03-07 through the subsequent evaluations.

The present invention relates to a new and distinct cultivar of Shasta daisy botanically known as *Leucanthemum* x *superbum* and hereinafter referred to by the cultivar name 'Cream Puff' or the new plant.

Asexual reproduction of the new cultivar by stem tip cuttings and shoot tip tissue culture at the same nursery in Zeeland, Mich. as early as the summer of 2013 has demonstrated that the new cultivar reproduces true to type with all of the characteristics of the original plant retained through successive generations of asexual propagation.

No plants of *Leucanthemum* 'Cream Puff' have been sold in this country, or anywhere in the world, prior to the filing of this application, nor has any disclosure of the new plant been made prior to the filing of this application with the exception of that which was disclosed or sold within one year of the filing of this application and was either derived directly or indirectly from the inventor.

BRIEF SUMMARY OF THE INVENTION

The new plant, *Leucanthemum* 'Cream Puff', is most closely compared to *Leucanthemum* 'Sonnenschein' and 'Banana Cream' U.S. Plant Pat. No. 23,181 in flower and *Leucanthemum* 'Snowcap' (not patented) and 'Whoops-a-Daisy' U.S. Plant Pat. No. 27,259 in habit. In test trials in Zeeland, Mich., 'Cream Puff' has more yellow flower buds and smaller flower diameter than 'Sonnenschein' and less yellow in the flower buds and flowers than 'Banana Cream'. 'Cream Puff' is also shorter, fuller, more compact and more rounded habit in flower due to more numerous axillary branching than either 'Sonnenschein' (not patented) or 'Banana Cream'. Compared with 'Whoops-a-Daisy' and 'Snowcap' the new plant is slightly smaller in habit and the flowers buds of 'Cream Puff' have more yellowish coloration. Compared with the female parent, the flowers buds of 'Cream Puff' have more yellowish coloration and the habit is fuller with flowers from the top of the plant down to the soil.

*Leucanthemum* 'Cream Puff' differs from all cultivars known to the inventor in the following combined traits:

1. Sturdy plants with dark green serrated foliage and strongly heavily-branched stems.
2. Mounded habit with flowering from the top of the plant to the ground.
3. Flowering with numerous axillary heads.
4. Double row of ray florets beginning light yellow in bud and becoming cream surrounding a gold center.
5. Freely flowering habit and repeating if deadheaded.

BRIEF DESCRIPTION OF THE PHOTOGRAPHS

The photographs of 'Cream Puff' demonstrate the overall appearance and landscape qualities of the new plant, including the unique traits. The colors are as accurate as reasonably possible with color reproductions. Ambient light spectrum, source, direction and temperature may cause the appearance of minor variation in color.

DETAILED BOTANICAL DESCRIPTION

Figure 1:
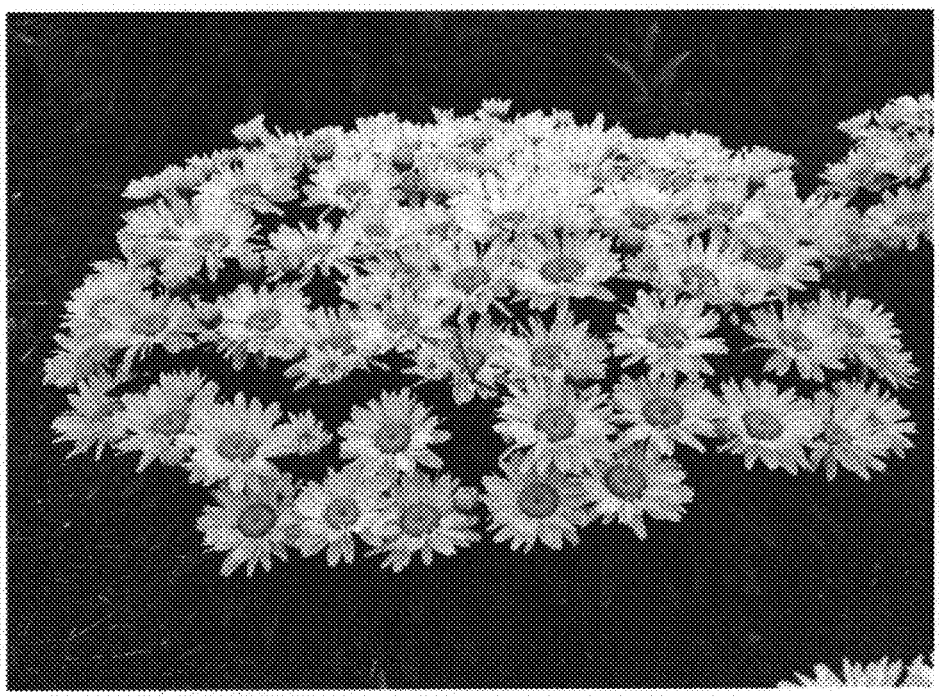
FIG. 1 Shows a two-year-old new plant at peak flowering with inflorescence covering the plant from nearly top to ground.
Figure 2:
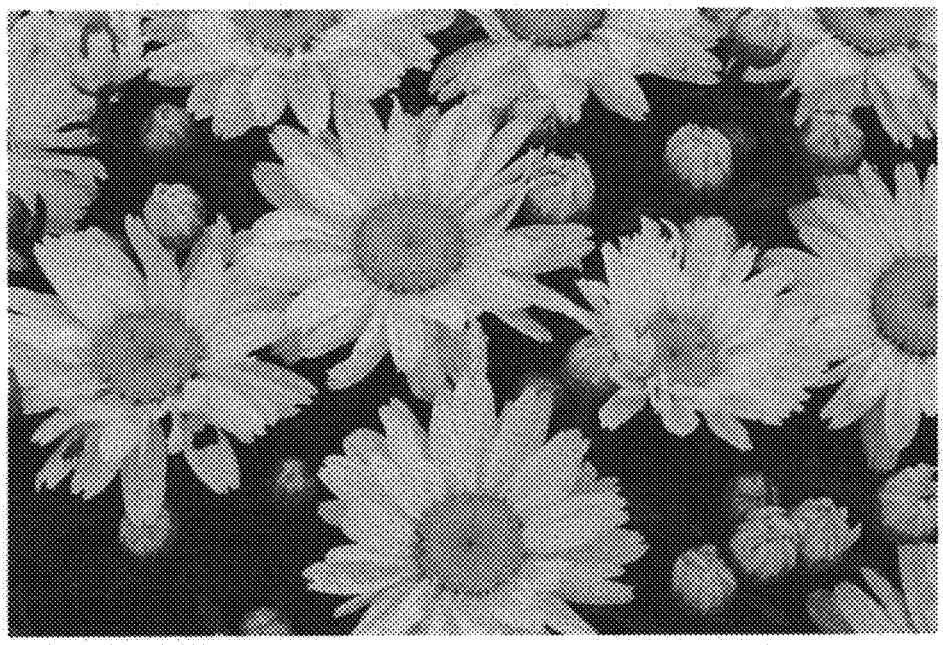
FIG. 2 Shows a close-up of the inflorescence and the buds.

The following descriptions and color references are based on the 2015 edition of The Royal Horticultural Society Colour Chart except where common dictionary terms are used. The new plant has not been observed in all possible environments and conditions. The phenotype of *Leucanthemum* 'Cream Puff' may vary with different growing conditions such as changes in temperature, light intensity, water availability, fertility, but without change in the genotype.

The plants used for description purposes were two years old and were grown in Zeeland, Mich. in a full-sun, loamy-sand trial plot environment with supplemental water and limited fertilizer as needed. Summer temperatures range from night lows of about 10° C. to daytime highs of about 34° C. Measurements and numerical values represent averages of trial plants.

Botanical classification: *Leucanthemum* x *superbum* (L. Burbank);

Parentage: The female parent is the unreleased proprietary hybrid known as K9-31-02; male parent unknown;

Habit: Herbaceous perennial with about eighty branched stems arising from rhizome base; each stem having three to four inflorescences each, rarely two; about 33 cm tall and 46 cm across with rounded top and sides; flowering from top to nearly soil level;

Roots: Fibrous, thin, heavily branched; root color nearest RHS 155D depending on soil type;

Propagation: Tip cuttings or tissue culture; about two weeks to produce roots from cutting; about 33 weeks to finish to flower in 3.8 liter pot depending on season;

Stems: About eighty main stems per plant, strong, upright and angled, 5.0 mm diameter at base, 50 cm tall; canaliculated, bispidulous; about 15 nodes, average internode length about 1.0 cm;

Stem color: Nearest RHS 138A;

Axillary branches: Three to four, rarely two per main stem; between 12 to 18.0 cm long and 3.0 to 4.0 mm diameter; at angles of about 45° from main stem;

Axillary branch color: Nearest RHS 138A;

Leaves: Apex acute; base sessile to attenuate, partially clasping; sparsely puberulent and margin serrated with variable teeth number from 7 to 24 per side, and size from less than 0.5 mm to 2.0 mm long; adaxial nearly microscopically puberulent and abaxial glabrous to microscopically puberulent; lowest leaves about 13.0 cm long and 3.7 cm wide, average about 8.5 cm long and 2.1 cm wide;

Leaf color: Adaxial color nearest RHS 139A, abaxial color between RHS 137A and RHS 137B; no fragrance detected;

Veins: Anastomosing, adaxial slightly raised, abaxial midrib costate;

Vein color: Abaxial midrib nearest RHS 138A and secondary veins same as surrounding leaf tissue; adaxial midrib nearest RHS 139B, secondary veins nearest RHS 139A;

Inflorescence: Capitate, about 260 per plant; primary inflorescence 8.5 cm across and 2.8 cm tall, axillary flowers 8.0 cm across and 2.5 cm tall; comprising about 45 ray florets and about 1100 disc florets; individual inflorescence lasting about three weeks on or cut from plant;

Fragrance: No fragrance detected;

Flowering period: Early summer (late June) to mid-summer in Michigan and repeating if deadheaded;

Peduncle: Strong, stiff; hispidulous to puberulent; round and longitudinal costate; 6.5 to 18.0 cm long and 3.0 to 4.0 mm diameter at base; upwardly to slightly outwardly;

Peduncle color: Nearest RHS 138A;

Bud: With ray florets still vertical, 2.5 cm across ray florets and 2.5 cm from base of phyllaries to apex of capitulum;

Bud color: Adaxial and abaxial ray floret coloration nearest RHS 1D;

Ray florets: About 45 per inflorescence; arranged around perimeter of capitulum in two overlapping rows; 3.7 cm long and 8.0 mm wide, lanceolate, glabrous; acute apex normally two clefts producing center lobe about 1.0 mm long and 1.5 mm wide at base, and two others on either side about 1.0 mm long and 1.2 mm wide at base; base attenuate, margin entire;

Ray floret color: As florets are first at 180° horizontal adaxial nearest RHS NN155B and abaxial between RHS NN155B and RHS NN155C; mature flower adaxial nearest RHS NN155C and abaxial nearest RHS NN155C;

Disc florets: About 1100 per inflorescence in center of capitulum, combined about 2.7 cm across and about 1.5 cm tall; individual floret about 8.0 mm tall and 1.2 mm wide, five tepals, about 3.0 mm long with acute apex, fused at base;

Disc floret color: Floret base between RHS 146 C and RHS 146B; apical 3 mm of florets RHS 13A;

Androecium: Only in disc florets; five stamens fused together around style;

*Anther*.—About 2.0 mm long and less than one mm wide, anther coloration nearest RHS 17A.

*Filaments*.—Fused together at apex, about 2.0 mm long and less than 0.1 mm diameter, filament coloration nearest RHS 2D.

Gynoecium: In ray florets and disc florets;

*Style*.—About 5.0 mm long and less than 1 mm diameter, split and curved at apical 1.0 mm; style coloration nearest RHS 154D.

*Stigma*.—Less than 0.5 mm diameter; stigma coloration between RHS 17D and RHS 17C.

Involucre: Made of about three layers of phyllaries averaging 48 per head; to 3.0 across and 0.5 cm tall;

Phyllaries: About 48 per head arranged in about three overlapping rows, 10.0 mm long and 3.0 mm wide; entire margin, apex obtuse, base truncate;

Phyllaries color: Between RHS 144A and RHS 144B on abaxial and adaxial center portions, on margin; distal phyllaries with a 1.0 mm wide transparent margin in the apical 3.0 mm; proximal phyllaries with apical third nearest RHS 145A;

Fruit: Achene, pointed at base and rounded at distal end with longitudinal color striations nearest RHS N200A and lighter than RHS 155D; about 3 to 4 mm long and 1.5 mm across; *Leucanthemum* 'Cream Puff' grows best with adequate moisture but can tolerate some dryness once established. It is tolerant of high temperatures of at least 36° and cold hardy to at least USDA zone 5 as well as strong wind and rain. Other disease or pest resistance beyond that common to Shasta daisy has not been observed.

I claim:

1. The new and distinct Shasta daisy plant, *Leucanthemum* 'Cream Puff' as herein shown and described.

* * * * *